United States Patent [19]

Altman

[11] Patent Number: 4,505,118

[45] Date of Patent: * Mar. 19, 1985

[54] INFRARED RADIATION COOLER FOR PRODUCING PHYSIOLOGIC CONDITIONS SUCH AS COMFORT OR HYPOTHERMIA

[76] Inventor: Gerald Altman, 2249 Commonwealth Ave., Newton, Mass. 02166

[*] Notice: The portion of the term of this patent subsequent to Mar. 9, 1999 has been disclaimed.

[21] Appl. No.: 354,142

[22] Filed: Mar. 5, 1982

Related U.S. Application Data

[63] Continuation of Ser. No. 138,494, Apr. 9, 1980, Pat. No. 4,318,722.

[51] Int. Cl.³ .......................................... F25B 21/02
[52] U.S. Cl. .............................................. 62/3
[58] Field of Search ................................. 62/3

[56] References Cited

U.S. PATENT DOCUMENTS 4,318,722 3/1982 Altman ............................. 62/3

Primary Examiner—Lloyd L. King
Attorney, Agent, or Firm—Morse, Altman & Dacey

[57] ABSTRACT

A condenser and transducer assemblage, within a gas filled protective enclosure, receives and processes a substantial proportion of mid and far infrared radiation from a subject in order to produce selected physiologic responses as a result of radiant cooling.

3 Claims, 6 Drawing Figures

INFRARED RADIATION COOLER FOR PRODUCING PHYSIOLOGIC CONDITIONS SUCH AS COMFORT OR HYPOTHERMIA

This is a continuation of application Ser. No. 138,494 now U.S. Pat. No. 4,318,722 filed on Apr. 9, 1980.

BACKGROUND OF THE INVENTION

1. Field of the Invention

The present invention relates to cooling devices and processes and, ore particularly, to the cooling of subjects in order to produce such physiologic conditions as comfort or hypothermia.

2. The Prior Art

Prior proposals for producing physiologic cooling by radiant heat exchange have had restricted application. In one prior proposal (U.S. Pat. No. 2,651,503, Sept. 8, 1953, C. A. Mills, System of Radiant Heat Exchanging), interior walls of a room have reflective surfaces which tend to direct infrared radiation to a heat sink with limited intermediate absorption and emission. This system is such that multiple reflections at the walls tend to result in intermediate absorption and emission even if it were possible to maintain high reflectivity of the walls under practical conditions. In another prior proposal (U.S. Pat. No. 3,282,267, Nov. 1, 1966, W. Eidus, Thermoelectric Hypothermia Instrument), cold panels are spaced about the patient in order to establish radiative heat exchange. This system is such that the panels must be unduly large or unduly close to the subject if appreciable radiation exchange is to be achieved. In a more recent proposal (U.S. Pat. No. 4,155,226, May 22, 1979, G. Altman, Infrared Cooler For Restricted Regions), intensified cooling of a restricted region is achieved by utilizing certain principles of geometrical optics to relate the subject region to a large infrared condenser and a small heat sink. The present invention takes advantage of certain mechanical-thermal-optical relationships to provide an infrared radiation cooler that is capable of operating effectively throughout a desired region, without being unduly close to the subject, to produce such physiologic conditions as comfort or hypothermia.

SUMMARY OF THE INVENTION

The primary object of the present invention is to provide devices and processes that are capable of efficaciously cooling a physiologic subject without contact by concentrating and transducing physiologic radiation with an optical condenser that communicates with the subject, a radiation absorber that communicates with the condenser, and a subfreezing heat sink that communicates with the radiation absorber, all within an enclosure having a front window and a contained gas that constitute propagation media for the physiologic radiation. The front window is in the form of an unsupported thin polymeric film, which is transparent to physiologic radiation and which itself is not an appreciable radiation emitter, in part because of its minimal axial dimension. However, because it is so thin, the front window is moisture permeable. Preferably, the moisture content of the contained gas (e.g. air) is maintained below the frost point by a gas dryer in order to prevent condensation on the radiation absorber during prolonged use. The enclosure effectively excludes dust from its interior.

Another object of the present invention is to provide, for incorporation in devices and processes of the foregoing type, so-called two (dish) and three (trough) dimensional condensers, which focus the physiologic radiation rearwardly so that the condenser generally is interposed between the window and the heat sink and the heat sink generally is interposed between the condenser and a back radiator, which dissipates thermal energy remotely from the subject. In effect, the devices and processes of the present invention reduce the mean radiant temperature configuration about the subject by redistributing thermal energy in the subject's environment.

A further object of the present invention is to divide the enclosure into two compartments, which are such that the forward compartment is defined by the window and the optical condenser, the rearward compartment contains the radiation absorber, and the front and rear compartments are open to each other at the rear of the condenser and in the vicinity of the radiation absorber. The relationships are such that the radiation is propagated in a gaseous path extending from the front window to the radiation absorber, but such that flow of gas between the two compartments is restricted. As a result, radiation flux from the window to the radiation absorber is maximal and convection between the window (which is at room temperature) and the radiation absorber (which is at subfreezing temperature) is minimal.

Other objects of the present invention will in part be obvious and will in part appear hereinafter.

The present invention thus comprises the devices and processes, together with their components, steps and interrelationships, which are exemplified in the present disclosure, the scope of which will be indicated in the appended claims.

BRIEF DESCRIPTION OF THE DRAWINGS

For a fuller understanding of the nature and objects of the present invention, reference is made to the following detailed description, which is to be read in connection with the accompanying drawings, wherein.

DETAILED DESCRIPTION OF THE PREFERRED EMBODIMENT

Introduction

Figure 1:
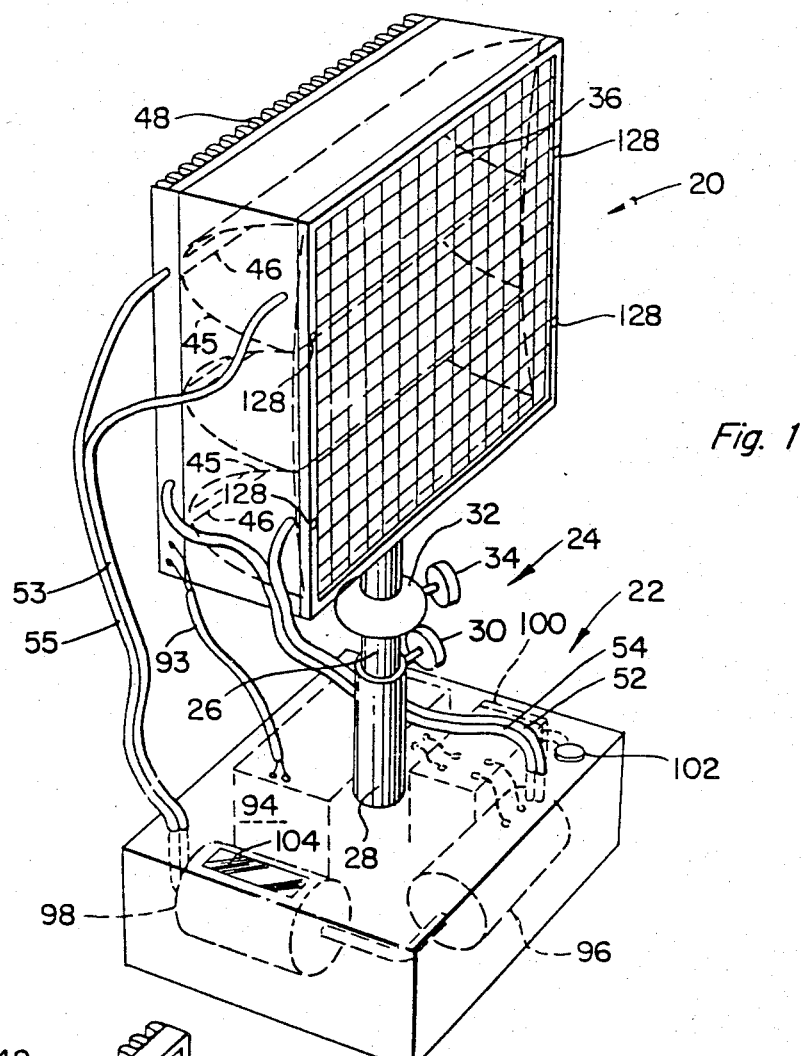
FIG. 1 is a perspective view of a radiation cooling device embodying the present invention.

The present invention, in effect, provides a strong negative radiation source for reducing mean radiant temperature with respect to a subject. In order to understand the phenomena involved, it is helpful to consider certain principles involved in the thermal exchange between a human subject and his environment as explained in a study by Fanger, P. O., *Thermal Comfort Analysis and Applications in Environmental Engineering*, McGraw-Hill, 1970. In general, there is a balance between heat dissipated from the human body and heat absorbed by the environment. At moderate environmental temperature, although the metabolic rate of the human body tends to maintain normal body temperature, there may be discomfort if the environment temperature is above or below certain limits, which depend upon a variety of factors. At low environmental temperature, the metabolic rate of the human body may be unable to maintain normal temperature so that hypothermia results.

The normal balance between metabolic heat dissipation and environmental heat absorption can be given by the following empirical equation, in which the variables are arranged in their usual order of decreasing magnitude:

$$f(H_m, I_{cl}, t_a, t_{mrt}, P_a, v, t_s, H_{lo}) = 0$$

where
$H_m$ = Internal heat production per unit body surface area
$I_{cl}$ = Thermal resistance of clothing
$t_a$ = Air temperature
$t_{mrt}$ = Mean radiant temperature
$P_a$ = Pressure of water vapor in ambient air
$v$ = Relative air velocity
$t_s$ = Mean skin temperature
$H_{lo}$ = Heat loss per unit body surface area by evaporation of sweat secretion The Fanger study indicates that the effect of mean radiant temperature on the human body is almost as great as the effect of air temperature if the relative air velocity is negligible. The mean radiant temperature, $T_{mrt}$, in relation to a given subject located at a given position, is defined as that uniform temperature of a black room (a room with black body walls, ceiling, and floor) which would result in the same heat loss by radiation from the subject as the actual room or space under consideration. In practice, the mean radiant temperature of a room with N surfaces, each of which is approximately isothermal, approximately grey (i.e. emittance=absorptance), and approximately diffusely reflecting, can be calculated from the following formula:

$$T_{mrt}^4 = T_1^4 F_{p-1} + T_2^4 F_{p-2} + \ldots + T_N^4 F_{p-N}$$

where $T_1$ to $T_N$ designate the temperatures and $F_{p-1}$ to $F_{p-N}$ are so-called space or angle factors that can be determined theoretically or empirically. Such space or angle factors, which depend on the dimensions, locations, and orientations of the surfaces of the room, are specified by reference to diagrams, examples of which are given in the Fanger study. The radiation cooler now to be described has an effective temperature (a function of its heat sink temperature) and an effective area (a function of its optical aperture), which are factors in determining the mean radiant temperature with respect to a subject in the environment this radiation cooler is intended to influence. Preferably, the front face of this radiation cooler is placed with respect to the subject at a distance at which both heat sink temperature and aperture size are significant factors in determining mean radiant temperature.

GENERAL DESCRIPTION OF THE EMBODIMENT OF FIGS. 1 AND 2

Figure 2:
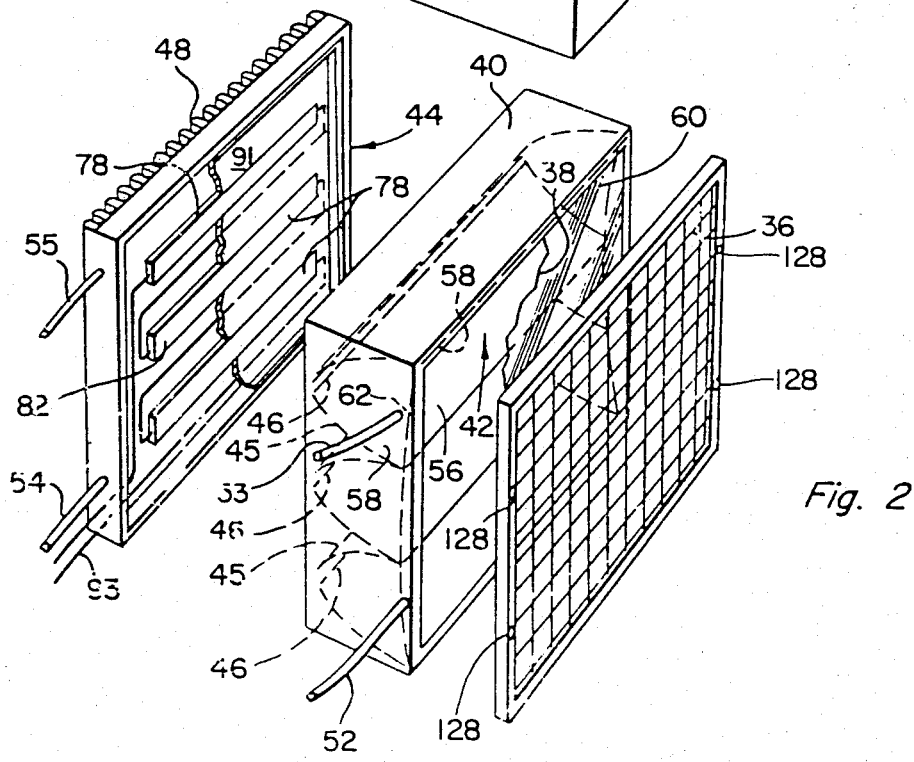
FIG. 2 is an exploded perspective view of certain components of the cooling device of FIG. 1.

With reference now to FIGS. 1 and 2, the illustrated radiation cooler comprises an upper concentrating and transducing assembly 20, a lower base and auxiliary assembly 22, and an intermediate adjustable stanchion or support 24. Support 24 includes upper and lower telescoping posts 26, 28, which can be fixed in extended or retracted condition by a suitable manually controlled knob and associated lock screw 30. Upper assembly 20 can be pivoted in any direction with respect to post 26 and can be fixed in any selected pivotal orientation by a universal junction 32 and a suitable manually controlled knob and associated lock screw 34.

The components of upper assembly 20 include a protective screen 36, an optical window 38, an outer housing 40, an optical condenser subassembly 42, and a radiation receiving and heat exchanging subassembly 44. Subassembly 42 has an array of condenser configurations 45, at the rear of which is an array of slots 46 extending substantially throughout the length of the array of condenser configurations. At the back of subassembly 44 is a finned radiator 48. Optical window 38 and finned radiator 48 constitute the front and back, respectively, of a gas filled enclosure having a forward compartment and a rearward compartment, which are open to each other only through slots 46. The gas within the enclosure preferably ranges in pressure between 5 and 25 pounds per square inch and preferably is composed of either air or nitrogen at approximately atmospheric pressure. The gas is circulated through the forward compartment via a pair of tubes 52, 53. The gas is circulated through the rearward compartment via a pair of tubes 54, 55. Tubes 52, 54 and 53, 55 communicate with components in base and auxiliary assembly 22 to be described below.

Window 38, is spaced away from the crossed strands of screen 36, by which it is protected against puncture and scratching by sharp objects. The strands, which are composed of a metal such as stainless steel or a polymer such as polyhexamethylene adipamide of the type sold by du Pont under the trade designation Nylon, are sufficiently thin and sufficiently spaced from each other to present a minor optical barrier, say less than two percent of the window area, to incoming physiologic infrared radiation. Window 38 is composed of an unsupported polymeric film that preferably is no more than 75 microns (3 mils) thick and for best results is no more than 12.5 microns (1 mil) thick. Preferred examples of the composition of this polymeric film are: polyolefins such as polyethylene, polypropylene, or polybutylene (unoriented, uniaxially oriented, or biaxially oriented); parylenes (polyxylylenes) such as poly-p-xylylene of the type sold by Union Carbide under the trade designation parylene N; and styrenes such as polystyrene. Preferably the composition and the thickness of this film are so related as to provide a transmissivity of at least 75% in the mid and far infrared, i.e. the physiologic infrared between 4 and 20 microns. Although window 38 is substantially at room temperature because of its physical contact with ambient air, its emission of infrared radiation is small because it is very thin. The theoretical basis for this effect is that radiant emission from a substantially transparent solid is a direct function of emissivity and thickness. In other words, radiant emission from a semi-transparent mass decreases as thickness decreases. See Blau, H. and H. Fischer, Radiative Transfer From Solid Materials, Macmillan, New York, pp. 8-23, 1962.

In accordance with the present invention, preferably each optical condenser configuration is of the type earlier called a tapered pipe or channel condenser. Smith, W. J., Modern Optical Engineering-the Design Of Optical Systems, McGraw-Hill Book Company, pp. 234, 235, 1966. More recently, this type of optical condenser has been called a nonimaging concentrator. Welford, W. T. and R. Winston, The Optics of Nonimaging Concentrators-Light and Solar Energy, Academic Press, 1978. In the illustrated embodiment, optical condenser subassembly 42 includes an array of three two dimensional or trough channel condensers, each of which has a pair of curved reflecting faces 56, 58 that, in axial cross section, converge rearwardly from a forward relatively wide rectangular entrance to a rearward relatively narrow exit. As stated above, the exit at the rear of each channel condenser, in effect, is a relatively narrow slot. Both the entrance and the exit extend substantially throughout the length of the trough by which they are defined. In effect, each face is the three-dimensional locus of a series of parallel linear increments developed about its direction of elongation. At the ends of each trough are a pair of reflecting end plates 60, 62, which are perpendicular to its direction of elongation. As illustrated, each reflector is in the form of a shaped polymer, composed for example of methyl methacrylate or polystyrene. The inner faces of the trough and its end plates are metallized, for example, vacuum coated with aluminum, silver, gold or other metal that is highly reflective in the mid and far infrared, the thickness of the coating typically ranging in thickness from 500 to 2500 angstrom units. As shown, in cross section, each surface of each trough is a conic section, for example, either ellipsoidal or paraboloidal, and preferably a compound conic section, for example, compound ellipsoidal or compound paraboloidal.

THE OPTICAL DESIGN OF THE CONCENTRATOR OF FIG. 3

Figure 3:
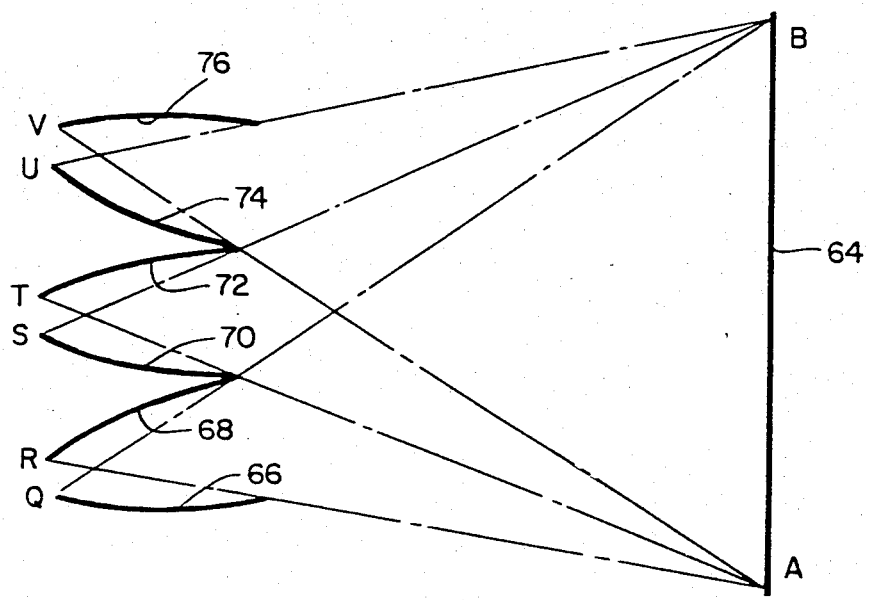
FIG. 3 is an optical diagram of a preferred condenser of the cooling device of FIG. 1.

An optical diagram of the preferred condenser, a compound ellipsoidal trough, is shown, by way of example, in FIG. 3. The theoretical design of a compound ellipsoidal concentrator is discussed in Welford, W. T. et al., The Optics of Nonimaging Concentrators—Light And Solar Energy, supra. Assuming that heavy line 64 is the dimension of a substantial region of the human body and considering the edge rays shown in phantom lines, reflecting surface 66 has an ellipsoidal curve with foci at B and R; reflecting surface 68 has an ellipsoidal curve with foci at A and Q; reflecting surface 70 has an ellipsoidal curve with foci at B and T; reflecting surface 72 has an ellipsoidal curve with foci at A and S; reflecting surface 74 has an ellipsoidal curve with foci at B and V; and reflecting surface 76 has an ellipsoidal curve with foci at A and U. It is to be noted that inner reflecting surfaces 68, 74 are different in shape from outer reflecting surfaces 66, 76. In effect, each of the three troughs is directed toward and focused on region 64, which is at a finite distance from window 38.

THE OPTICAL-THERMAL-MECHANICAL DESIGN OF FIGS. 2 AND 4

Figure 4:
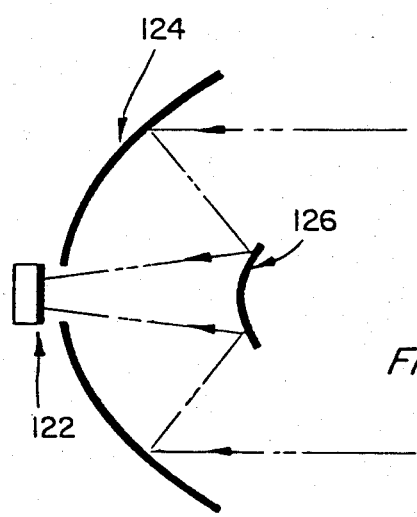
FIG. 4 is an exaggerated electrical and mechanical, side elevation, partly broken away, of the heat sink and heat exchanger subassembly of the cooling device of FIG. 1.

Radiation receiving and heat exchanging subassembly 44 includes an array of three parallel radiation-receiver and heat-transfer strips 78, which are registered with the array of elongated slots 46 at the rear of the trough reflectors of optical condenser subassembly 42. As shown in FIG. 4, the body 80 of strip 78 is composed of a highly conductive metal such as copper or aluminum. At the front face 82 of strip 78 is a coating or surfacing having very high, preferably at least 90%, radiation absorptivity in the physiologic wavelength range of mid and far infrared radiation. Face 82 of strip 78 is operationally electrostatic, i.e. is not a component of an electrically active loop. In other words, the heat sink is electromotively isolated so as to be free of power dissipation that is significant in relation to infrared radiation received from the subject. Preferably, the heat conductivity from front face 82 to the body and through the body is as high as possible so that heat generated in front face 82 is transferred into and through body 80 substantially instantaneously. Face 82, for example, is composed of a metal black, such as gold black, platinum black or chrome black, directly in contact with body 80 or directly in contact with a gold or other noble metal substrate in contact with the body. Gold black, particularly, has a very high absorptivity. Harris, L., R. T. McGinnies, The Preparation and Optical Properties of Gold Blacks, Journal Of The Optical Society of America, 38:582-589, 1948. In one form, back radiator 48 is composed of aluminum and its outer face is black anodized for high radiative emissivity and high convective conductivity. Mechanically and thermally connected between strips 78 and back radiator 48 is an array of thermoelectric modules 84 that extend longitudinally throughout the lenghts of the strips.

Each thermoelectric module incorporates an array of small thermoelectric elements of the Peltier type, in which a ceramic cold plate 86 and ceramic hot plate 88 are separated by pairs of N and P semiconductor elements. Where the current direction is as shown at I, the N and P elements are connected by electrically conducting elements 90 at the cold plate and the P and N elements are connected by electrically conducting elements 92 at the hot plate. Electrical current flow from an N element to a P element causes predetermined cooling at cold plate 86 and electrical current flow from a P element to an N element causes predetermined heating at hot plate 88. In order to isolate front face 82 from thermal exchange other than by radiation through window 38, the inner faces of the back and side walls of radiator 48 are coated with a thermal insulator 91 such as polyurethane foam. Accordingly the rear compartment, except for front faces 82, is bounded by thermal insulating material, the rear walls of the condensing troughs being composed of an insulating polymer.

As shown in FIG. 1, the thermoelectric modules are energized by direct current through leads 93 from a power supply 94 in lower assembly 22.

THE ELECTRICAL-MECHANICAL DESIGN OF LOWER ASSEMBLY 22-FIG. 1

Also in lower assembly 22 are an electrically energized gas pump 96, a transparent cartridge 98 containing a granular dessicant charge, an electrical controller 100, and an on-off switch 102. Controller 100 is connected electrically both to power supply 94 and to pump 96, as shown by dashed lines in FIG. 1. When controller 100 is energized by switch 102, pump 96 is energized initially and, following a predetermined delay, power supply 94 is energized thereafter. The delay enables pump 96 to circulate the gas in upper assembly 20 through the dessicant in cartridge 98 via tubes 52, 54 and 53, 55 for a sufficiently long period to dry the gas before the thermoelectric array starts to operate. The arrangement is such that circulation of the gas through the dessicant charge is continued until the power supply is deenergized by deactuating on-off switch 102.

In one form, the dessicant is an absorbent, for example, an anhydrous salt such as calcium sulfate impregnated with a minor concentration of calcium chloride and mixed with a minor concentration of cobalt chloride. The calcium chloride acts as a catylist to maximize moisture absorption capacity. The cobalt chloride, which is blue when dry and pink when moist, acts as an indicator to assure that the dry or moist condition of the dessicant is apparent on inspection. Such materials are sold commercially by W. A. Hammond Drierite Company under the trade designation "Drierite". A window 104 in the housing of lower assembly 22 permits an operator to note the condition of the dessicant at all times. In another form, the dessicant is an adsorbent, for example, a dehydrated zeolite, i.e. a crystalline aminosilicate. Other absorbing or adsorbing agents, for example, include activated alumina, barium oxide, lithium chloride, and silica gel.

THE ALTERNATIVE EMBODIMENT OF FIG. 5

Figure 5:
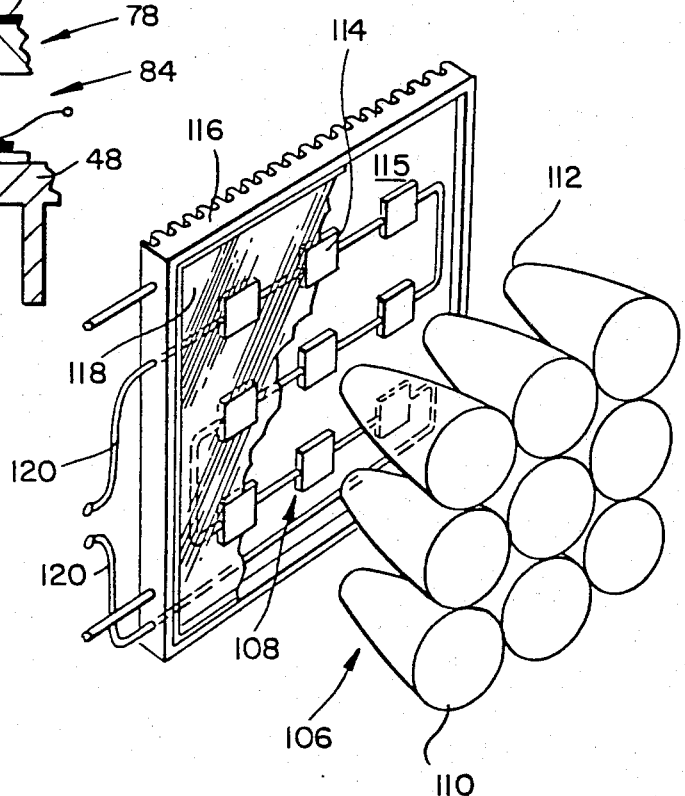
FIG. 5 is a perspective view of an alternative preferred condenser and associated heat exchanger subassembly for incorporation in the cooling device of FIG. 1.

FIG. 5 illustrates an alternative condenser assembly 106 and an alternative receiving-transducing assembly 108, which are substituted, respectively, for condenser assembly 42 and receiving-transducing assembly 44 in an alternative embodiment analogous to the embodiment of FIGS. 1 and 2. As shown, condenser assembly 106 includes an array of three dimensional or dish reflectors 110, each having a reflecting face that, in axial cross-section, converges from a forward relatively wide circular entrance to a rearward relatively narrow circular exit. Preferably, each reflecting face, in cross-section, is in the shape of a compound conic, e.g. compound ellipsoid or compound paraboloid, i.e. the locus of an ellipsoidal or parabolic curve developed about an axis other than its focal axis. Best results are achieved with the compound ellipsoidal configuration. The structural materials of reflectors 106 are analogous to the structural materials of optical condenser sub-assembly 42. Receiving-transducing assembly 108 includes an array of radiation-receiver and heat-transfer elements 114, which are registered with exits 112 of array of condensers 106. The structural materials of elements 114 are analogous to the structural materials of elements 78, as described in reference to FIG. 4. Array of elements 114 are mounted at the inner back face of a radiator 116 and are encapsulated in a thermal insulator 118 except for their front faces in the manner described in reference to radiator 48 of FIG. 2. Array of elements 114 is energized electrically via leads 120, 120.

THE ALTERNATIVE EMBODIMENT OF FIG. 6

Figure 6:
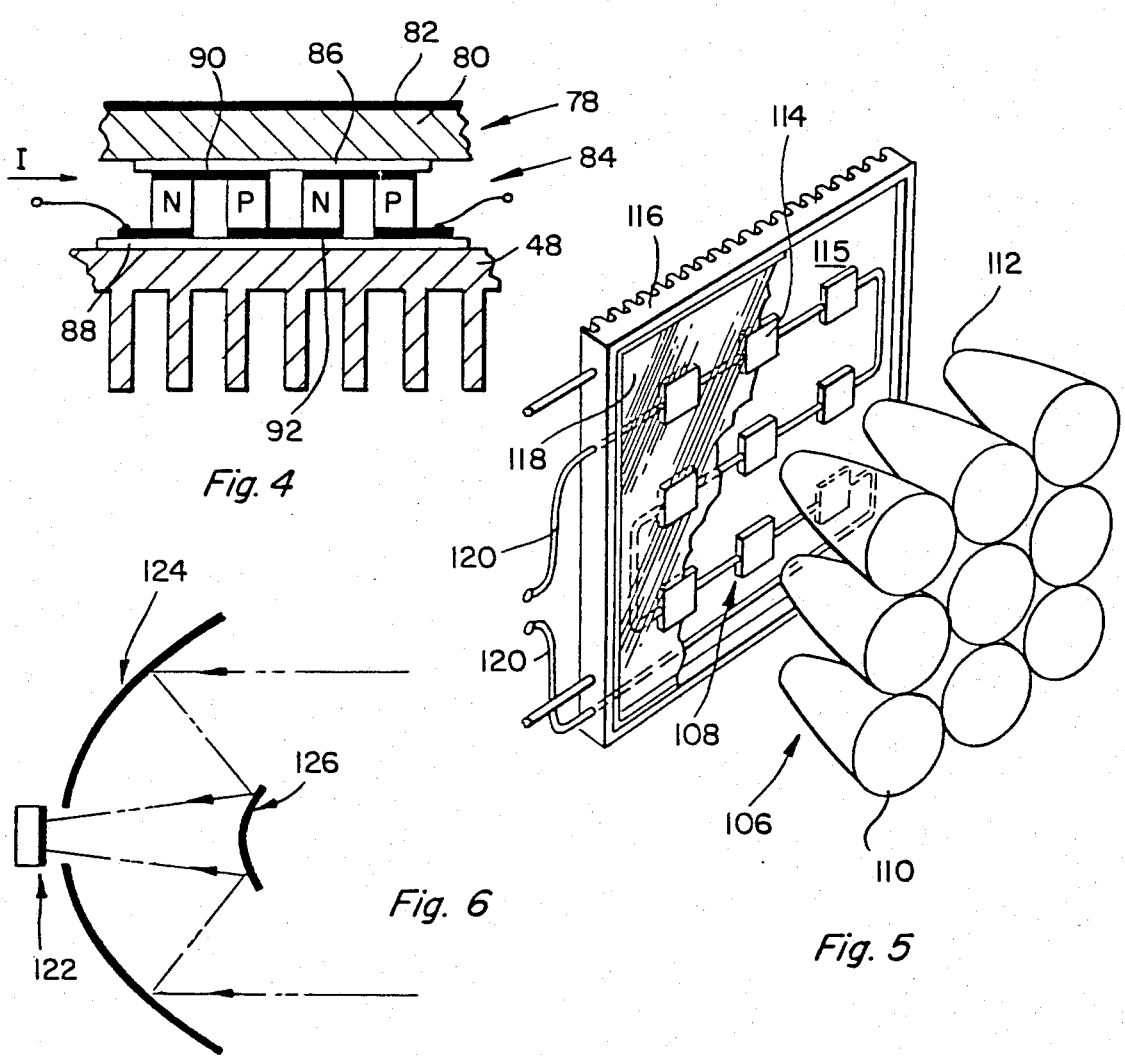
FIG. 6 is an optical diagram of another condenser for incorporation in the cooling device of FIG. 1.

FIG. 6 illustrates an alternative condenser configuration comprising a rearward primary spherical reflector 124 having a center aperture and a forward secondary hyperbolic reflector 126. Reflector 124 is of extended dimension and reflector 126 is of restricted dimension so that incoming radiation is directed from reflector 124 and via reflector 126 to a radiation receiving and transducing subassembly 122 at the aperture in reflector 124. The materials of which reflectors 124 and 126 and of which subassembly 122 are composed are analogous to the materials of which their counterparts are composed in the previously described embodiments. In an alternative embodiment of the present invention, an array of condensers of the type shown in FIG. 6 is substituted for the array of condensers of FIG. 5.

OPERATION AND CONCLUSION

Prior to use of the radiation cooler of FIG. 1, it can be assumed that ambient moisture will have permeated window 38 and that the moisture concentration within upper assembly 20 will equal the moisture concentration of the environmental air. In order to start operation, the radiation cooler is directed toward a subject to be cooled and start stop button 102 is pressed. Air within the forward compartment is circulated through tubes 52, 53 and air within the rearward compartment is circulated through tubes 54, 55 for a period sufficiently long to reduce the frost point of the air within both compartments to lower than the operating temperature of the front faces of the radiation receivers. Thereafter, the thermoelectric elements are energized. As a result, the temperature of the front faces of the radiation receivers is reduced to a subfreezing operating level and heat transferred to radiator 48 is dissipated by external convection. Since the openings between the forward and rearward compartments are small and since the air in both compartments is dry, interchange of air between the compartments is minimal and convection between front window 38 and the front faces of the radiation receivers is minimal. Radiator 48 is thermally isolated by the insulating coating on its inner walls. All of the operating elements are protected against dust accumulation by the enclosure of which window 38 is a part. Screen 36 is removably attached to the forward face of the enclosure by set screws 128 so that window 38 can be cleaned periodically. The condition of the dessicant within cartridge 98 can be observed through window 104 so that the dessicant cartridge can be replaced when needed.

Since certain changes may be made in the foregoing disclosure without departing from the scope of the invention herein, it is intended that all matter shown in the accompanying drawings or described in the foregoing specification be interpreted in an illustrative and not in a limiting sense.

What is claimed is:

1. A radiation cooler for localized non-contact cooling of a human subject, comprising:
  (a) a forward array of radiation concentrators, a rearward heat sink means, and an array of radiation receiving surface elements therebetween;
  (b) said array of radiation concentrators having a forward array of extended apertures and a rearward array of restricted apertures and having inner surfaces that are highly reflective in the mid and far infrared radiation region;
  (c) said forward array of extended apertures being operative to receive infrared radiation from said human subject;
  (d) said array of radiation receiving surface elements being registered and optically communicating with said rearward array of restricted apertures;
  (e) an array of Peltier type thermoelectric elements having cold junctions conductively connected to said array of receiving surface elements and hot junctions conductively connected to said heat sink means;
  (f) said heat sink means including a metallic conductor that has an extensive outer convective surface;
  (g) an electrical system for energizing said array of thermoelectric elements such that said cold junctions in operation are at subfreezing temperature;

(h) means for preventing the deposition of frost on said radiation receiving surface elements;
(i) said radiation cooler, with respect to an axis directed forwardly and rearwardly, being greater in lateral extent than in longitudinal extent.

2. The radiation cooler of claim 1 wherein said concentrators are characterized by a compound ellipsoidal dish configuration.

3. The radiation cooler of claim 1 wherein said concentrators are characterized by a compound ellipsoidal trough configuration.

* * * * *